United States Patent [19]
Satomi et al.

[11] 3,961,935
[45] June 8, 1976

[54] SYNERGISTIC HERBICIDAL COMPOSITION COMPRISING O-METHYL OR O-ETHYL-O-(3-METHYL-6-NITROPHENYL)-N-SECONDARY-BUTYLPHOSPHOROTHIOAMIDATE AND A PHENOXY-TYPE HERBICIDE

[75] Inventors: Takeo Satomi, Nishinomiya; Naganori Hino, Toyonaka,, Japan

[73] Assignee: Sumitomo Chemical Company, Limited, Osaka, Japan

[22] Filed: Nov. 9, 1973

[21] Appl. No.: 414,574

[30] Foreign Application Priority Data
Nov. 10, 1972 Japan............................. 47-113129

[52] U.S. Cl.................................. 71/87; 71/108; 71/109; 71/110; 71/116; 71/117; 71/118
[51] Int. Cl.². ............................................. A01N 9/36
[58] Field of Search................................. 71/117, 87

[56] References Cited
UNITED STATES PATENTS
3,549,349   12/1970   Gramlich.............................. 71/110
3,682,614   8/1972   Hack et al............................ 71/110

OTHER PUBLICATIONS

Satomi et al., "Herbicidal O-(5-methyl-2-nitrophenyl)" etc.; (1972) CA 76, No. 153,375v.

Primary Examiner—Glennon H. Hollrah
Attorney, Agent, or Firm—Sughrue, Rothwell, Mion, Zinn & Macpeak

[57] ABSTRACT

A herbicidal composition comprising O-methyl or O-ethyl-O-(3-methyl-6-nitrophenyl)-N-secondary-butylphosphorothioamidate and a phenoxy-type herbicide represented by the formula:

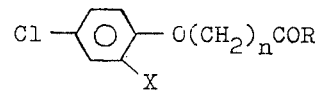

wherein X, R and $n$ are hereinafter defined, and a herbicidally acceptable inert carrier is disclosed.

6 Claims, No Drawings

SYNERGISTIC HERBICIDAL COMPOSITION COMPRISING O-METHYL OR O-ETHYL-O-(3-METHYL-6-NITROPHENYL)-N-SECONDARY-BUTYLPHOSPHOROTHIOAMIDATE AND A PHENOXY-TYPE HERBICIDE

BACKGROUND OF THE INVENTION

1. Field of the Invention

The present invention relates to a herbicidal composition of a mixture of O-methyl-O-(3-methyl-6-nitrophenyl)-N-secondary-butylphosphorothioamidate (hereinafter referred to as the compound A) or O-ethyl-O-(3-methyl-6-nitrophenyl)-N-secondary-butyl-phosphorothioamidate (hereinafter referred to as the compound B) and a phenoxy-type herbicide represented by the formula:

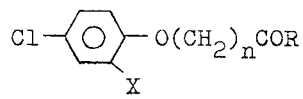

wherein X represents a chlorine atom or a methyl group, R represents a hydroxy group, a $C_1$ to $C_4$ alkoxy group, an amino group or an anilino group, and $n$ represents an integer of 1 to 3; the herbicidal composition displaying a remarkable synergistic effect that any one cannot expect from the single use of each of the components.

2. Description of the Prior Art

One of the various herbicides for rice plant, 2-methyl-4-chlorophenoxyacetate (hereinafter referred to as MCP), has prominent effects to broad-leaved weeds [i.e. monochoria (*Monochoria vaginalis* Presl), false pimpernel (*Lindernia Pyxidaria*), tooth cup (*Rotala indica Koehne*)], but, on the other hand, has a little herbicidal effect to grassy weeds, and moreover has a little herbicidal effect to perennial weeds [i.e. perennial nutsedge sp. (*Cyperus serotinus*), arrowhead sp. (*Sagittaria pygmaea*), hardstem bulrush (*Scirpus juncoides*)].

Each compound A and B has particularly prominent herbicidal activity to grassy weeds [i.e. barnyard grass (*Echinochloa Crus-galli*)], but has a little herbicidal effect to broad-leaved weeds [i.e. monochoria (*Monochoria vaginalis* Presl), false pimpernel (*Lindernia Pyxidaria*), tooth cup (*Rotala indica Koehne*)] at their large stage, and moreover has a little herbicidal effect to the perennial weeds [i.e. perennial nutsedge sp. (*Cyperus serotinus*), arrowhead sp. (*Sagittaria pygmaea*), hardstem bulrush (*Scirpus juncoides*)].

As the results of extensive studies, present inventors have found that each mixtures containing one of phenoxy-type compounds and the compound A or the compound B have very excellent herbicidal activities to both broad-leaved weeds and to grassy weeds, and particularly each combined herbicides has prominent effects to the perennial weeds which are not controlled by the single use of each of the components, i.e., MCP, the compound A or the compound B.

These facts described above show that present combined herbicides have better advances as a herbicide.

SUMMARY OF THE INVENTION

As a rule, a herbicide which does not kill all the weeds in question cannot exhibit sufficient economical effect. For instance, if a certain kind of weeds survives, it will propagate an inflict damage on the crops and the economical effect of the herbicide will be halved. Accordingly, it is desirable that herbicides have a wide herbicidal spectrum, i.e. properties capable of killing a wide variety of weeds. Because of the recent situation of labor insufficiency, it is also desired to develop herbicides such that they will be highly effective even if used at any time that workers could have time, that is to say, herbicides having a wide range of the suitable period of treatment.

DETAILED DESCRIPTION OF THE INVENTION

We have been working for the development of excellent herbicides. The compound A or compound B, which is an organic phosphorous compound discovered by us and which is one of the components of the herbicidal composition according to the present invention, exhibits a powerful herbicidal effect on the growth of most weeds by pre-emergence treatment. By post-emergence treatment, however, the herbicidal effect is weakened as weeds grow larger, particularly the effect on broad-leaved weeds is sharply reduced, and the herbicidal spectrum becomes narrow. Thus, these compounds are herbicides having a narrow range of the suitable period of treatment. Although we studied mixed agents of each of these compounds with various other herbicides to obviate such defects, most of combinations exhibited a mere added effect or offsetting effect. However, a combination with MCP which is one of the phenoxy-type compounds, i.e., party of the present invention, gave a very good result. Thereafter, in studying phenoxy-type acid derivatives, we have found that mixtures with a phenoxy-type compound represented by the above-described general formula, similarly to the mixture with MCP, have a surprising synergistic herbicidal effect. Examples of such phenoxy-type compounds are:

1. 2-methyl-4-chlorophenoxyacetic acid
2. ethyl 2-methyl-4-chlorophenoxyacetate
3. allyl 2-methyl-4-chlorophenoxyacetate
4. 2-methyl-4-chlorophenoxyacetamide
5. 2-methyl-4-chlorophenoxyaceto orthochloroanilide
6. ethyl 2-methyl-4-chlorophenoxypropionate
7. ethyl 2,4-dichlorophenoxyacetate
8. 2,4-dichlorophenoxyacetic acid triethanol amine These phenoxy-type compounds are known as herbicides. As their characteristics of action, high efficacy for broadleaved weeds and somewhat less efficacy for gramineous weeds, slow action etc. can be enumerated.

Results obtained by mixture agents of a phenoxy-type compound with the compound A or B are shown by examples. On the 18th day after rice planting in a rice field, the field was treated with the following mixture agents and on the 30th day after the treatment the herbicidal efficacy was assessed. The results are shown in Table 1.

Table 1

| Amount of MCP used (active ingredient grams/are) | Dry weight of the remaining weeds in the treated area to that in the untreated area (%) | | | | | |
|---|---|---|---|---|---|---|
| | Amount of Compound A used (active ingredient grams/are) | | | Amount of Compound B used (active ingredient grams/are) | | |
| | 8 | 4 | 0 | 8 | 4 | 0 |
| 2 | 3 | 9 | 50 | 1 | 6 | 50 |
| 1 | 10 | 31 | 65 | 7 | 24 | 65 |

Table 1-continued

| Dry weight of the remaining weeds in the treated area to that in the untreated area (%) | | | | | | |
|---|---|---|---|---|---|---|
| Amount of Compound A used (active ingredient grams/are) | | | Amount of Compound B used (active ingredient grams/are) | | | |
| 0 | 25 | 49 | 100 | 20 | 37 | 100 |

These results were analyzed by the method of Colby mentioned in Weeds, vol. 15, pages 20-22. In the Colby's method, when the expected value calculated by the formula:

$$\left(\begin{array}{c}\text{Expected value from}\\ \text{the mixture agent (\%)}\end{array}\right) = \frac{\left(\begin{array}{c}\text{Observed value}\\ \text{from } X \text{ agent}\\ \text{only (\%)}\end{array}\right) \times \left(\begin{array}{c}\text{Observed value}\\ \text{from } Y \text{ agent}\\ \text{only (\%)}\end{array}\right)}{100}$$

is larger than the observed value from the mixture agent, it is judged that there is a synergetic effect. According to this formula, in the mixed use of 8 g/are of the compound A and 2 g/are of MCP, for example, Expected value = $\frac{25 \times 50}{100}$ = 13%

Observed value = 3%, and therefore the expected value is larger than the observed value. Also, in the mixed use of 8 g/are of the compound B and 2 g/are of MCP, Expected value = 10%

Observed value = 1%, and therefore the expected value is larger than the observed value. Accordingly, it is judged that there is an evident synergetic effect in both cases. Also, in herbicidal experiments for upland field weeds, an evident synergetic effect was observed particularly when weeds were treated during the growth period. The present mixture comprising MCP and compound A or compound B shows both excellent herbicidal activity and little phytotoxicity on rice plants. Therefore, the combined herbicide has the best characters as a herbicide.

Although the reason for this synergetic effect is not known for certain, the following supposition may be possible: In the case of treatment before germination of weeds, the organic phosphorous compound A or B, which is one of the components of the composition according to the present invention, has a powerful herbicidal effect essentially non-selectively on all weeds. However, once weeds have grown, it is considered, resistant weeds have a certain recovering means to weaken the efficacy of the agent, but the phenoxy-type compound hinders the recovery by such a manner as the disturb metabolic pathways of this recovery means. Thus, by the mixed use of these two kinds of compounds a powerful synergetic action can be produced.

As explained above, the mixed compositions of the compound A or B and the phenoxy-type compounds display a remarkable synergetic effect by strengthening the herbicidal effect of the respective components. This synergetic effect not only strengthens the herbicidal effect but also enlarges the range of the herbicidal spectrum and the suitable period of treatment, shortens the time required to kill weeds, and increases the selectivity for crops than weeds by varying the mixing ratio. Thus, the present invention is very useful from the viewpoint of agriculture.

The areas to which the herbicidal compositions according to the present invention can be applied include fields of rice and other cereals, beans, vegetables, orchards, turfs, fields of wood plant seedlings and non-farming areas, and in any of these places the herbicidal compositions of the present invention display excellent herbicidal action.

In the actual use of the herbicidal compositions according to the present invention, they can be used in any form of granules, wettable powers, emulsifiable concentrates, fine granules, dusts, etc. The suitable mixing ratio of the two kinds of compounds is 1 weight part of the compound A or B to 0.1 ~ 5.0, more preferably 0.1 ~ 0.5, weight parts of the phenoxy-type compound represented by the above-mentioned general formula. The total amount of active ingredients in the formulated herbicides ranges from 1% to 90%, preferably 1% to 50% by weight in the actual use.

In the actual preparation of the compositions, the solid carriers used are, for example, talc, bentonite, clay, kaolin, diatomaceous earth, vermiculite, slaked lime, etc.; the liquid carriers are, for example, benzene, alcohols, acetone, xylene, methylnaphthalene, dioxane, cyclohexanone, etc.; and the emulsifiers are, for example, alkylsulfates, alkylsulfonates, polyethylene glycol ethers, polyhydric alcohol esters, etc.

Examples of formulation to form the herbicidal compositions according to the present invention are shown in the following:

FORMULATION EXAMPLE 1

20 weight parts of the compound A, 5 weight parts of ethyl 2-methyl-4-chlorophenoxyacetate, 5 weight parts of a polyoxyethylene acetylarylester surface active agent and 70 parts of talc are thoroughly ground and mixed to produce a wettable powder.

FORMULATION EXAMPLE 2

20 weight parts of the compound B, 5 weight parts of 2,4-dichlorophenoxyacetate, 10 weight parts of a polyethylene glycol ether active agent, 25 weight parts of cyclohexanone and 40 weight parts of xylene are intimately mixed to obtain an emulsifiable concentrate.

FORMULATION EXAMPLE 3

7 weight parts of the compound B, 1.0 weight part of allyl 2-methyl-4-chlorophenoxyacetate, 5.5 weight parts of a salt of lignin sulfonic acid, 86.5 weight parts of clay are thoroughly ground and mixed, and intimately kneaded with water. The mixture is formed into granules and then dried to obtain a granular agent.

The invention is explained in further detail by the following example, but not restricted thereto.

EXAMPLE 1

A concrete pot, 50 cm × 50 cm in size, placed outdoors was filled with rice field soil and water was added to the soil to make it rice field-like. Rice seedlings at the five-leaves stage were transplanted to the soil. On the 15th day after the transplanting, the water-covered soil was treated with the granules produced according to Formulation Example 3 at the rate of 300 grams/are. On the 30th day after the treatment, the weeds were pulled out and the dry weight was measured. The ratio of this dry weight to the dry weight of weeds in the untreated area are shown in Table 2. The weeds naturally occurred were *Echinochloa Crus-galli* Beauv., *Monochoria vaginalis* Presl, *Dopatrium junceum* Ham., *Rotala indica* Koehne, *Lindernia Pyxidaria* L., *Cyperus compressus* L., *Eleocharis acicularis* R., etc. The herbicidal efficacy and the phytotoxicity were evaluated and the markings were represented by the numerals from 0 to 10 as shown in the following:

| | Action on plants |
|---|---|
| 0 | Same as in the untreated area |
| 1–2 | Very slight |
| 3–4 | Slight |
| 5–6 | Medium |
| 7–8 | Heavy |
| 9–10 | Extremely heavy |

In Table 2 the phenoxy-type compounds are shown by the numbers given to the previously exemplified compounds.

Table 2

| Compounds tested and amounts of application (g/are) Phenoxy-type compound | Compound A or B | Phytotoxicity on rice | Barnyard grass | Broad-leaved weeds |
|---|---|---|---|---|
| (2), 2 g + A, 10 g | | 1 | 10 | 10 |
| (2), 2 g + B, 10 g | | 1 | 10 | 10 |
| (2), 2 g | | 1 | 2 | 6 |
| (3), 2 g + A, 10 g | | 0 | 10 | 10 |
| (3), 2 g + B, 10 g | | 0 | 10 | 10 |
| (3), 2 g | | 0 | 2 | 6 |
| (5), 3 g + A, 10 g | | 0 | 10 | 10 |
| (5), 3 g + B, 10 g | | 0 | 10 | 10 |
| (5), 3 g | | 0 | 2 | 6 |
| (6), 2 g + A, 10 g | | 0 | 10 | 10 |
| (6), 2 g + B, 10 g | | 0 | 10 | 10 |
| (6), 2 g | | 0 | 2 | 6 |
| | A, 10 g | 0 | 7 | 3 |
| | B, 10 g | 0 | 7 | 3 |

EXAMPLE 2

A concrete pot of 50 cm × 50 cm placed outdoors was filled with paddy field soil, and water was added thereto to make it paddy field-like. Then rice seedlings at the four leaves stage, the seedlings of *Cyperus serotinus*, *Sagittaria pygmaea* and *Scirpus juncoides* at four leaves stage were transplanted thereto and, furthermore, tubers of *Sagittaria pygmaea* and *Cyperus serotinus* were planted therein. On the 12th day after transplanting, the water-covered soil was treated with the granules produced by the same way as Formulation Example 3 at the rate of 300 g/are. On the 30th day after the treatment the weeds were pulled out and the dry weight was measured. The ratio of this dry weight to the dry weight of weeds in the untreated area are shown in Table 3. The herbicidal efficacy and the phytotoxicity were evaluated and the markings were represented by the numerals from 0 to 10 as shown in Example 1.

In Table 3 the phenoxy-type compounds are shown by the numbers given to the previously exemplified compounds.

Table 3

| Compounds tested and amounts of application (g/are) Phenoxy-type compound | Compound A or B | Phytotoxicity on rice | Herbicidal efficacy on Cyperus serotinus | Sagittaria pygmaea | Scirpus juncoides |
|---|---|---|---|---|---|
| (2), 2 g + A, 10 g | | 1 | 7 | 8 | 8 |
| (2), 2 g + B, 10 g | | 1 | 8 | 8 | 8 |
| (2), 2 g | | 2 | 0 | 2 | 4 |
| (3), 2 g + A, 10 g | | 0 | 8 | 8 | 8 |
| (3), 2 g + B, 10 g | | 0 | 8 | 9 | 9 |
| (3), 2 g | | 0 | 0 | 3 | 5 |
| (5), 3 g + A, 10 g | | 0 | 7 | 7 | 7 |
| (5), 3 g + B, 10 g | | 0 | 7 | 7 | 7 |
| (5), 3 g | | 0 | 0 | 2 | 3 |
| (6), 2 g + A, 10 g | | 0 | 7 | 8 | 7 |
| (6), 2 g + B, 10 g | | 0 | 8 | 8 | 8 |
| (6), 2 g | | 0 | 0 | 2 | 3 |
| | A, 10 g | 0 | 1 | 1 | 1 |
| | B, 10 g | 0 | 1 | 1 | 1 |

While the invention has been described in detail and with reference to specific embodiments thereof, it will be apparent to one skilled in the art that various changes and modifications can be made therein without departing from the spirit and scope thereof.

What we claim is:

1. A synergistic herbicidal composition consisting essentially of a herbicidally effective amount of the mixture of O-methyl or O-ethyl-O- (3-methyl-6-nitrophenyl)-N-secondary-butylphosphorothiomidate and a phenoxy-type herbicide represented by the formula:

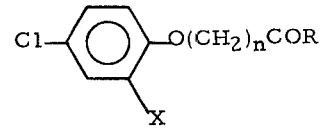

wherein X represents a chlorine atom or a methyl group, R represents a hydroxy group, $n$ is an integer of 1 to 3, said butylphosphorothioamidate being present in an amount of one weight part for 0.1 – 0.5 weight parts of said phenoxy-type compound, and a herbicidally acceptable inert carrier.

2. A herbicidal composition of claim 1, wherein the composition is in a form of an emulsifiable concentrate, wettable powder, granule, dust, oil spray or aerosol.

3. A herbicidal composition of claim 1, wherein the total amount of active ingredients being 1 to 90%.

4. The herbicidal composition of claim 1, which consists essentially of O-ethyl-O-(3-methyl-6-nitrophenyl)-N-secondary-butylphosphorothioamidate and 2,4-dichlorophenoxy acetic acid.

5. A method for controlling weeds, which comprises applying thereto an effective amount of the herbicidal composition of claim 1.

6. The method of claim 5, wherein said composition consists essentially of O-ethyl-O(3-methyl-6-nitrophenyl)-N-secondary-butylphosphorothioamidate and 2,4-dichlorophenoxy acetic acid as active ingredients.

* * * * *